United States Patent
Lorenzen et al.

(10) Patent No.: US 9,562,919 B2
(45) Date of Patent: Feb. 7, 2017

(54) APPARATUS AND METHOD FOR HANDLING SAMPLE TUBES AND LABORATORY SYSTEM

(71) Applicant: Roche Diagnostics Operations, Inc., Indianapolis, IN (US)

(72) Inventors: Tom Lorenzen, Kisdorf (DE); Reto Andrin Meier, Schwaebisch Hall (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 246 days.

(21) Appl. No.: 14/294,197

(22) Filed: Jun. 3, 2014

(65) Prior Publication Data
US 2014/0363259 A1 Dec. 11, 2014

(30) Foreign Application Priority Data
Jun. 11, 2013 (EP) .................................... 13171536

(51) Int. Cl.
*B65G 65/32* (2006.01)
*G01N 35/04* (2006.01)

(52) U.S. Cl.
CPC ....... *G01N 35/04* (2013.01); *G01N 2035/0406* (2013.01); *G01N 2035/0462* (2013.01); *G01N 2035/0465* (2013.01)

(58) Field of Classification Search
CPC ............................................ G01N 2035/0406
See application file for complete search history.

(56) References Cited

U.S. PATENT DOCUMENTS 4,223,778 A * 9/1980 Kontz ................ B65G 47/1471
198/389
6,325,129 B1 12/2001 Wright et al.
(Continued)

FOREIGN PATENT DOCUMENTS

EP 2148204 B1 1/2010
EP 2472267 A2 7/2012
(Continued)

OTHER PUBLICATIONS

Lorenzen, Tom, "Bildverarbeitung Oberfliissig," 2011, pp. 59-61, with English translation.

*Primary Examiner* — Sean E Conley
*Assistant Examiner* — Benjamin Whatley
(74) *Attorney, Agent, or Firm* — Roche Diagnostics Operations, Inc.

(57) ABSTRACT

An apparatus for handling sample tubes is presented. The apparatus comprises a sample tube tray, a sample tube individualizer, a first conveyor, a second conveyor, a sample tube buffer, and a sample tube rack inserter. The sample tube tray stores sample tubes in bulk commodity. The sample tube individualizer sequentially unloads single sample tubes from the sample tube tray and sequentially provides the unloaded sample tubes to the first conveyor. The first conveyor conveys the sample tubes to the sample tube buffer. The sample tube buffer buffers the sample tubes provided by the first conveyor and provides buffered sample tubes to the second conveyor with a predeterminable, constant, sample tube rate. The second conveyor conveys the sample tubes to the sample tube rack inserter. The sample tube rack inserter inserts the sample tubes into a sample tube rack.

12 Claims, 4 Drawing Sheets

(56) References Cited

U.S. PATENT DOCUMENTS

| | | | |
|---|---|---|---|
| 6,581,355 B1 * | 6/2003 | Yuyama | B65B 5/103 141/168 |
| 7,504,067 B2 | 3/2009 | Itoh | |
| 7,931,861 B2 | 4/2011 | Kitagawa | |
| 2003/0194349 A1 * | 10/2003 | Carey | B01L 3/508 422/63 |
| 2004/0131499 A1 * | 7/2004 | Okada | G01N 35/025 422/64 |
| 2004/0144618 A1 * | 7/2004 | McDonald | B65G 15/14 198/389 |
| 2007/0158163 A1 * | 7/2007 | Kritzinger | B65G 15/58 198/397.06 |
| 2007/0269342 A1 * | 11/2007 | Kitagawa | G01N 35/04 422/64 |
| 2010/0233754 A1 * | 9/2010 | Guex | G01N 35/02 435/29 |
| 2011/0002760 A1 * | 1/2011 | Pedrazzini | B65G 47/1471 414/222.07 |
| 2012/0171078 A1 * | 7/2012 | Kaneko | G01N 35/025 422/65 |

FOREIGN PATENT DOCUMENTS

| | | |
|---|---|---|
| WO | 02/086514 A2 | 10/2002 |
| WO | 2009/092710 A1 | 7/2009 |

* cited by examiner

APPARATUS AND METHOD FOR HANDLING SAMPLE TUBES AND LABORATORY SYSTEM

CROSS-REFERENCE TO RELATED APPLICATIONS

This application is a continuation of EP 13171536.9, filed Jun. 11, 2013, which is hereby incorporated by reference.

BACKGROUND

The present disclosure generally relates to an apparatus and a method for handling sample tubes and a laboratory system.

Laboratory sample distribution systems are used to distribute samples or specimens such as, for example, blood samples, contained in sample tubes between various different laboratory stations or specimen-processing instruments, such as pre-analytical stations, analytical stations and post-analytical stations.

The sample tubes are typically supplied in a bulk commodity. To achieve an efficient handling, the sample tubes have to be inserted into sample tube racks.

Therefore, there is a need to provide an apparatus and a method for handling sample tubes and a laboratory system that is highly flexible and that offers a high processing performance.

SUMMARY

According to the present disclosure, an apparatus, laboratory system and method for handling sample tubes is presented. The apparatus can comprise a sample tube tray. The sample tube tray can store sample tubes in bulk commodity. The apparatus can further comprise a sample tube individualizer and a first conveyor. The first conveyor can convey the sample tubes to the sample tube buffer. The sample tube individualizer can sequentially unload single sample tubes from the sample tube tray and sequentially provide the unloaded sample tubes to the first conveyor. The apparatus can also comprise a second conveyor and a sample tube buffer. The sample tube buffer can buffer the sample tubes provided by the first conveyor and can provide buffered sample tubes to the second conveyor with a predeterminable, constant, sample tube rate. Finally, the apparatus can comprise a sample tube rack inserter. The second conveyor can convey the sample tubes to the sample tube rack inserter. The sample tube rack inserter can insert the sample tubes into a sample tube rack Accordingly, it is a feature of the embodiments of the present disclosure to provide an apparatus and a method for handling sample tubes and a laboratory system that is highly flexible and that offers a high processing performance. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The apparatus can comprise a sample tube tray. The sample tube tray can store sample tubes in bulk commodity. The sample tube tray may form a well, wherein the sample tubes intended for processing may be filled or dumped into the sample tube tray in an unordered fashion. The sample tube tray may for example be dimensioned to store about 50 to about 500 sample tubes.

The apparatus can further comprise a sample tube individualizer. The sample tube individualizer can sequentially unload single sample tubes comprised in the sample tube tray and can sequentially provide the unloaded sample tubes to a first conveyor. The sample tube individualizer may be adapted such that sample tubes filled into the sample tube tray can basically be processed in a first-in-first-out scheme. The first conveyor can sequentially convey the sample tubes provided by the sample tube individualizer to a sample tube buffer.

The sample tube buffer can buffer the sample tubes provided by the first conveyor and provide buffered sample tubes to a second conveyor with a given, for example, constant, sample tube rate. The sample tube buffer may, for example, have a buffer capacity of about 5 to about 20 sample tubes.

The second conveyor can convey the sample tubes to a sample tube rack inserter with the sample tube rate defined by the sample tube buffer.

The first and the second conveyor may have horizontal conveying directions and the tubes may be conveyed in any orientation, for example, in a horizontal or vertical position. In one embodiment where the tubes are conveyed horizontally, the tubes can be conveyed in an longitudinal orientation, such as along a direction defined by the long axis of the sample tubes.

The sample tube rack inserter can insert the sample tubes into a sample tube rack. The sample tube rack may be a conventional sample tube rack used in laboratory automation. In other embodiments, the sample tubes may be loaded into a sample puck for holding single sample tubes.

The sample tubes may be conventionally closed by caps. The sample tubes may be provided to the first conveyer and/or to the second conveyor such that the sample tubes can be initially conveyed in a random conveying direction, namely being either cap first or cap last. To deal with this degree of freedom, the apparatus may comprise at least one conveying direction determiner to determine the conveying direction of a respective sample tube. The apparatus may further comprise at least one conveying direction changer functionally coupled to the conveying direction determiner and the first and/or the second conveyor, wherein the conveying direction changer can change the conveying direction, especially by approximately 180 angular degrees, such that each sample tube can be provided to the sample tube buffer and/or the sample tube rack inserter in a defined conveying direction. The unified conveying direction can simplify the further processing of the sample tubes.

If the conveying direction determiner can determine the conveying direction of a respective sample tube placed on the second conveyor, sample tubes placed on the second conveyor not having the defined conveying direction may be reinserted into the sample tube tray, for example, by a slide extending between the second conveyor and the sample tube tray. Alternatively, the conveying direction changer (or one of the conveying direction changers) may be functionally coupled to the conveying direction determiner assigned to the second conveyor, wherein this conveying direction changer can change the conveying direction on the second conveyor, by about 180 angular degrees, such that the sample tubes can be provided to the sample tube rack inserter in the defined conveying direction.

It can be possible that a first conveying direction determiner and a corresponding first conveying direction changer can be assigned to the first conveyor and that additionally a second conveying direction determiner and a corresponding second conveying direction changer can be assigned to the second conveyor. In case that the first direction change operation fails and/or that an unintentional direction change happens after sample tube has passed the first conveying direction determiner, it can be possible to correct this fault.

The first and/or second conveyor may comprise a first and a second belt, the first and the second belt extending in parallel along a conveying direction and spaced by a given belt distance. The belt distance can be dimensioned such that a sample tube may be placed on the two belts in longitudinal direction. The belt distance may lie in the range of about 0.5 cm to about 5 cm. The first and the second belt may be driven with an identical belt speed, for example, by a common driving cylinder.

The conveying direction changer may comprise a rotatable leg or rotatable post, the leg or post can be arranged between the first and the second belt. The leg may have a width smaller than the given belt distance. The leg when rotating can change the conveying direction of a sample tube placed on top of the leg. The leg when rotating can also rotate the sample tube placed on the belts. In a non-active state of the leg, the leg may be placed at a level under the conveying level defined by the belts.

The conveying direction changer may rotate the leg with a predetermined rotating speed profile. At the beginning, i.e. at angles smaller than or equal to zero angular degrees relative to horizontal (leg parallel to the conveying direction), the leg may have a rotating speed of about 30 revolutions per minute (rpm). This relatively low rotating speed can prevent the sample tube from being kicked off by the leg when the leg initially gets in contact with the sample tube. Between zero angular degrees and approximately 40 angular degrees, the rotating speed may be increased up to about 75 rpm. Between about 41 angular degrees and about 100 angular degrees, the rotating speed may be kept constant at about 75 rpm. Between about 101 angular degrees and approximately 135 angular degrees, the rotating speed may be reduced to approximately zero rpm. The leg can then be rotated back to an initial position at for example, about −120 angular degrees starting with about 60 rpm, accelerating to about 150 rpm and slowing down to about 0 rpm. This rotating speed profile can ensure a safe yet fast rotating of the sample tube.

The sample tube rack inserter may comprise a pusher to apply a push force to a sample tube, for example, to a cap of the sample tube, to be inserted into a sample tube rack. The pusher may perform a vertical movement. The pusher may, for example, be incorporated as a motor actuated plunger or piston, the plunger pushing or pressing the sample tube into the sample tube rack or sample puck.

The pusher may comprise a pushing head. The pushing head may comprise an opening, for example, in the form of a blind hole, to house an upper portion of the sample tube (or a cap placed on top of the sample tube), which sample tube is to be inserted into the sample tube rack. A concave shaped surface of the pushing head can surround the opening. The opening may be arranged in the center of the concave shaped surface or may be arranged out of the center of the concave shaped surface. The concave shaped surface can guide the upper portion of the sample tube during an insertion process such that the upper portion of the sample tube can glide along the concave surface towards the opening and can be finally housed, at least partially, in the opening. The push force may, for example, be applied to the sample tube or to the upper portion of the sample tube by an upper bounding surface of the opening. By the pushing head, it can be possible to vertically align the sample tube during an insertion process, such that the sample tube may be inserted into the sample tube rack as vertical as possible.

The pusher may apply a predetermined push force profile to the sample tube. At the beginning, a maximum push force (largest available push force) may be applied to the sample tube. After reaching a first insertion position, the push force may be reduced by about 50% to 100%. The first insertion position may be reached if about 90% to 98% of a complete insertion path of the sample tube into the sample tube rack is reached. After that, about 80% to 95% of the maximum push force may be applied to the sample tube until a final insertion position is reached. The final insertion position may be mechanically defined, for example, by form fit between the sample tube and the sample tube rack. This push force profile can cause a smooth yet safe insertion process.

The sample tube rack inserter may comprise a feed hopper or funnel. The hopper can receive sample tubes from the second conveyor and can center the received sample tubes with respect to a dedicated opening of sample tube rack. The pusher, or plunger, may apply the push force to the sample tube after the sample tube is centered by the hopper. The pusher, or plunger, may be inserted into or penetrate the hopper during an insertion operation. The hopper may be movable in a horizontal and/or vertical direction.

The hopper may have a vertical opening. The hopper may, for example, be closed only on three vertical sides. The vertical opening can enable a movement of the hopper in a horizontal direction after the sample tube is inserted into the sample tube rack. If the sample tube is closed by a cap having a diameter larger than a diameter of the sample tube, a vertical up movement of the hopper may unintentionally remove the sample tube from sample tube rack, if a filling opening of the hopper has a diameter smaller than the diameter of the cap.

The sample tube rack inserter may comprise a sloped guide arranged between the second conveyor and the hopper. The sloped glide can be sloped such that sample tubes provided by the second conveyor can move towards the hopper by gravitational force.

The sample tube rack may have two or more openings horizontally spaced for inserting corresponding sample tubes. The second conveyor, the sample tube rack inserter, and/or the pusher may be respectively horizontally moved relative to the sample tube rack, such that a sample tube may be inserted into a corresponding opening of the sample tube rack without needing to move the sample tube rack. Alternatively, the rack can be moved and the second conveyor, the sample tube rack inserter and/or the pusher can remain stationary, for example, where the sample tube rack is replaced with a sample puck that can be directly moved away toward other components of an analytical system by a conveyor.

The first and the second conveyor may have same or different vertical levels.

The sample tube buffer may comprise a sloped storage plane. The first conveyor may provide sample tubes to the storage plane. The storage plane may be sloped such that sample tubes provided by the first conveyor can move towards a defined conveying position by gravitational force. The storage plane may be geometrically dimensioned to store a given number of sample tubes.

The sample tube buffer may comprise a vertical conveyor; the vertical conveyor can sequentially load single sample tubes from the conveying position, convey the loaded sample tubes in a vertical direction, and sequentially provide the loaded sample tubes to the second conveyor at the defined sample tube rate. The vertical conveyor can function as a sample tube elevator supplying sample tubes at a defined sample tube rate.

The sample tube buffer may monitor a number of sample tubes placed on the storage plane, i.e., a filling level of its buffer. This may, for example, be done by a suitable sensor such as, for example, a light barrier. The sample tube buffer may signal to the sample tube individualizer and to the first conveyor if more than a given threshold value of sample tubes are placed on the storage plane, such that the sample tube individualizer and the first conveyor can stop operating if the buffer is full.

Since the sample tube tray can store the sample tubes in bulk commodity, the sample tube individualizer may not be able to unload a corresponding sample tube in every unloading step. Therefore, the sample tube individualizer can typically provide sample tubes at an unpredictable sample tube rate but having an average which can be typically constant. If this average is larger than an average of sample tubes supplied to the second conveyor by the sample tube buffer, it can be possible to supply the sample tubes to the second conveyor at a fixed rate. If the buffer is full, the supply to the buffer can be temporarily stopped until a lower buffer threshold value is reached. This can simplify the processing and enhances the processing performance.

The sample tube individualizer may comprise a vertical chain conveyor having a number of chain members; each chain member can unload single sample tubes from the sample tube tray and can provide the unloaded sample tubes to the first conveyor.

The laboratory (automation) system can comprise at least one laboratory station. The laboratory stations may be pre-analytical, analytical and/or post-analytical stations, for processing sample tubes and/or samples contained in the sample tubes. The laboratory stations may operate sample tube rack based, i.e., sample tubes can be provided to the laboratory stations comprised in sample tube racks.

The laboratory (automation) system can further comprise an apparatus for handling sample tubes as described above. The apparatus can form the front end of the laboratory (automation) system. The sample tubes can be provided in a completely unsorted bulk commodity. The sample tubes may just be dumped into the sample tube tray, wherein the apparatus can provide filled sample tube racks for further processing by the laboratory stations.

The method for handling sample tubes or operating the apparatus for handling sample tubes can comprise: storing sample tubes in bulk commodity in a sample tube tray, sequentially unloading single sample tubes from the sample tube tray at a non-constant sample tube rate, for example, by the sample tube individualizer, buffering the unloaded sample tubes, for example, by the sample tube buffer, and sequentially inserting the buffered sample tubes into a sample tube rack at a predeterminable, constant, sample tube rate, for example, by the sample tube rack inserter.

A number of sample tubes actually buffered may be monitored, and if more than a given threshold value of sample tubes are actually being buffered, the sequentially unloading single sample tubes from the sample tube tray may be paused or stopped until a lower buffer threshold value can be reached.

Figure 1:
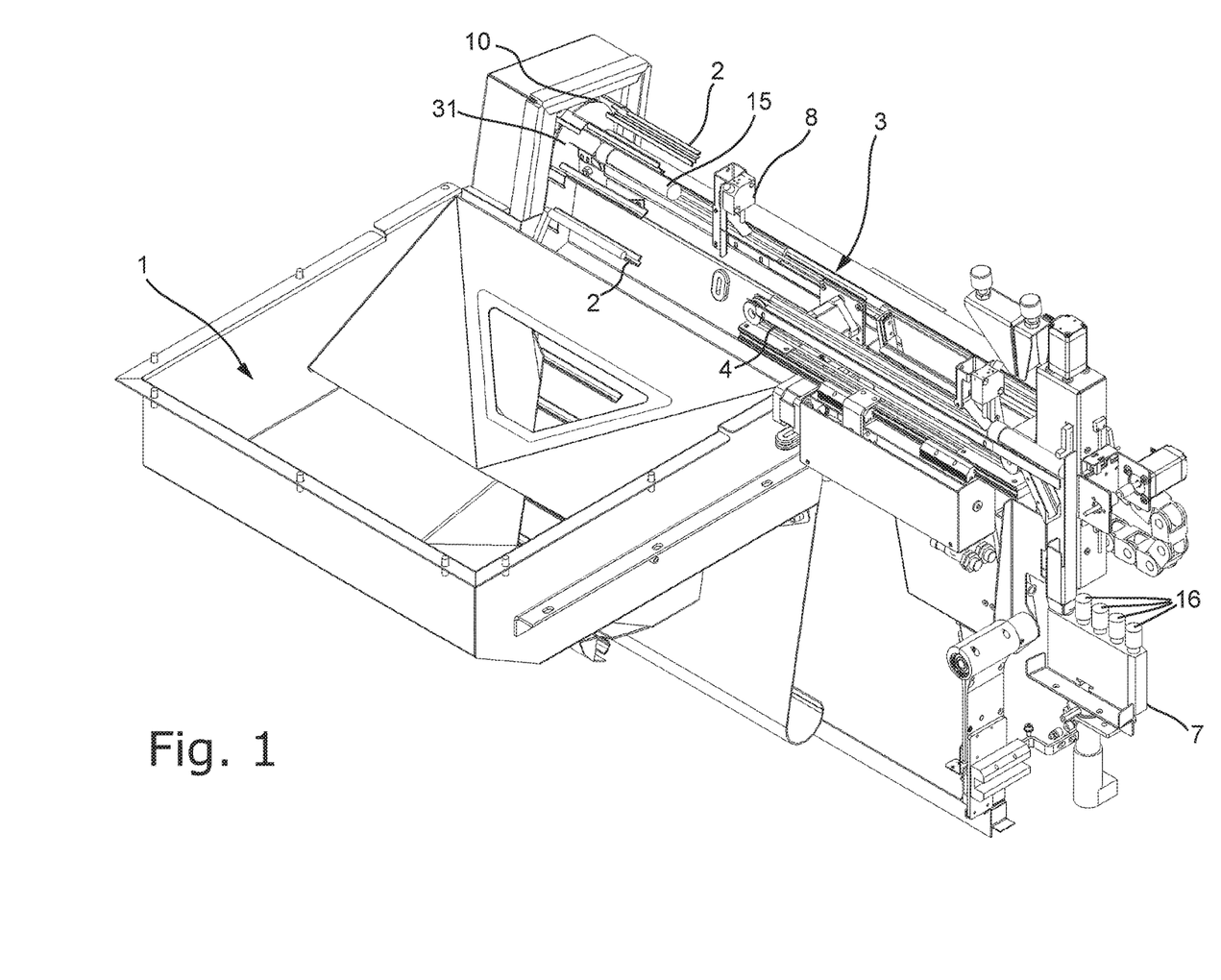
FIG. 1 illustrates an apparatus for handling sample tubes from a first perspective according to an embodiment of the present disclosure.

Referring initially to FIG. 1, FIG. 1 shows an apparatus for handling sample tubes 15 from a first perspective. As depicted in FIG. 1, the apparatus can comprise a sample tube tray 1. The sample tube tray 1 can store sample tubes 15 in bulk commodity. The sample tube tray 1 can form a well, wherein the sample tubes 15 intended for processing can be dumped into the sample tube tray 1 in an unordered fashion. The sample tube tray 1 can be dimensioned to store about a few hundred sample tubes 15. The sample tube tray 1 may be covered by a removable or pivotable coverage (not shown).

The apparatus can further comprise a sample tube individualizer in the form of a vertical chain conveyor having a number of chain members 2. Each chain member 2 can unload a single sample tube 15 from the bottom of the sample tube tray 1 and can provide the unloaded sample tube 15 to a first belt conveyor 3.

The chain members 2 can be attached to a chain 10. The chain 10 can be guided and driven by two gear wheels, wherein only an upper gear wheel 31 is shown. The upper gear wheel 31 can rotate around a horizontal axis lying in a conveying direction of the first conveyor 3. When the chain 10 rotates around the upper gear wheel 31, the corresponding chain members 2 can rotate around a horizontal axis such that the sample tubes 15 can be dumped off of the chain members 2 and can fall on the first conveyor 3.

Figure 2:
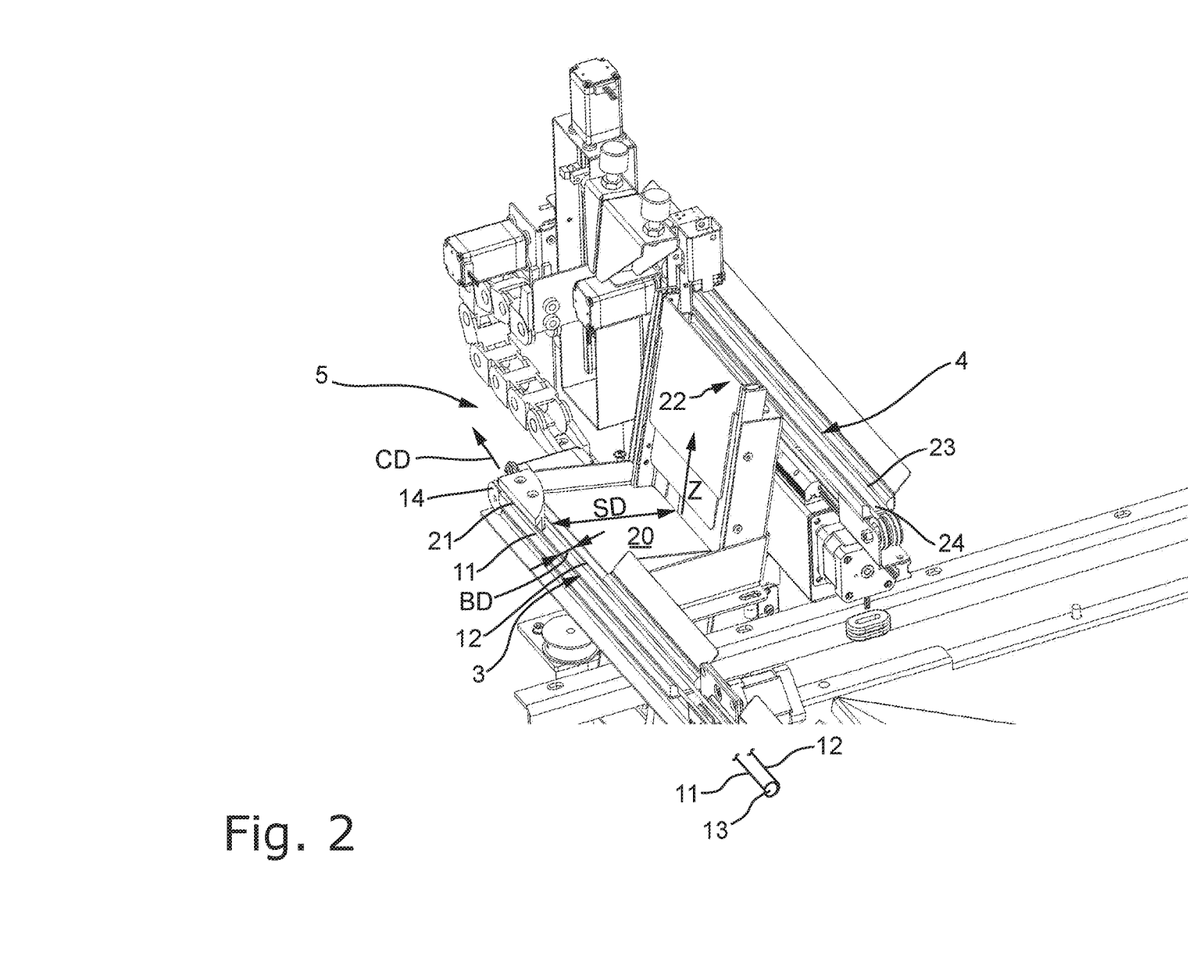
FIG. 2 illustrates the apparatus for handling sample tubes from a further perspective according to an embodiment of the present disclosure.

The first conveyor 3 can comprise a first rubber band or belt 11 (see FIG. 2) and a second rubber band or belt 12 (see FIG. 2), the first and the second belt 11 and 12 extending in parallel along a conveying direction CD and can be spaced by a given belt distance BD. The belt distance BD can be chosen smaller than a diameter of processed sample tubes 15. The first and the second belt 11 and 12 can be driven by rolls 13 and 14 and can have an identical conveying speed.

The sample tubes 15 can be closed by caps 16. Due to the properties of the sample tube individualizer 2, it may not be possible to provide the sample tubes 15 to the first conveyer 3 such that the sample tubes can have a given conveying direction, i.e., cap first or cap last.

Since further processing steps can require that the sample tubes are provided cap last, the apparatus can comprise a conveying direction determiner 8 to determine the conveying direction of a respective sample tube 15 and a conveying direction changer 9 functionally coupled to the conveying direction determiner 8 and the first conveyor 3, wherein the conveying direction changer 9 can change the conveying direction such that each sample tube can be provided to a sample tube buffer 5 cap last.

In one embodiment, the conveying direction determiner 8 can sample a height profile of a conveyed sample tube 15. Typically, caps 16 can have a larger diameter than sample tubes 15. Thus, if a sample tube 15 closed by a cap 16 is conveyed cap first, the sampled height can decrease if the cap has passed the conveying direction determiner 8. If a sample tube 15 is conveyed cap last, the sampled height can increase as soon as the cap passes the conveying direction determiner 8. Thus, by analyzing the height profile, the conveying direction determiner 8 can be able to determine the conveying direction.

In other embodiments, the conveying direction determiner 8 may comprise a camera and image processing to determine the conveying direction. Image processing may be useful if the cap 16 has basically the same diameter than the sample tube 15.

The conveying direction determiner 8 and the conveying direction changer 9 can be functionally coupled. If the conveying direction determiner 8 determines a "wrong" conveying direction, the conveying direction changer 9 can be signaled by the conveying direction determiner 8 to change the conveying direction. The time point of signaling can be chosen such that the corresponding sample tube 15 can be within an operating range of the conveying direction changer 9.

The conveying direction changer 9 can comprise a rotatable central leg 17, the central leg 17 (see FIG. 4) arranged between the first and the second belt 11 and 12, the central leg 17 having a width smaller than the given belt distance BD, and the central leg 17 when rotating changing the conveying direction of a sample tube 15 placed on top of the central leg 17. Adjacent to the central leg 17, two supporting legs 18 and 19 can be arranged, the supporting legs 18 and 19 supporting a sample tube 15 in a rotating operation.

Figures 4, 5, 6:
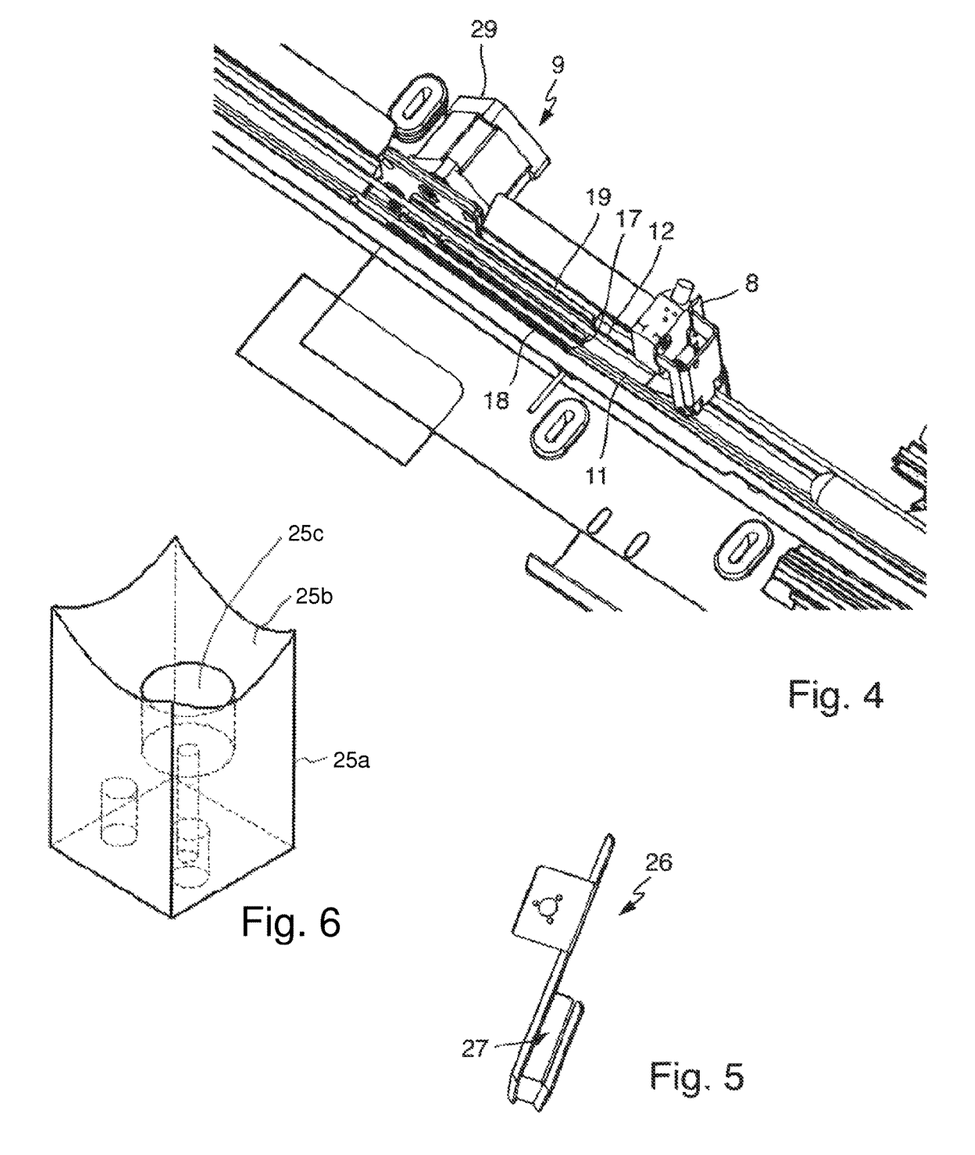
FIG. 4 illustrates a conveying direction changer of the apparatus depicted in FIGS. 1 to 3 according to an embodiment of the present disclosure.
FIG. 5 illustrates a feeding hopper of the apparatus depicted in FIGS. 1 to 3 according to an embodiment of the present disclosure.
FIG. 6 illustrates an embodiment of a pusher having a specific pushing head according to an embodiment of the present disclosure.

The legs 17 to 18 can respectively be rotated by a stepper motor 29. The legs 17 to 19 can be rotated from an initial position back to the initial position with an angle speed profile "slow, accelerating from slow to fast, constant fast, slowing down to zero, reverse" during a direction changing operation.

Due to the direction changing operation, if necessary, the sample tubes 15 can be respectively provided to the buffer 5 in a unified conveying direction.

The buffer 5 can comprise a sloped storage or buffer plane 20. The sample tubes 15 provided by the first conveyor 3 can be wiped of the first conveyor by a deflector 21 and can be directed to storage plane 20. The storage plane can be sloped such that sample tubes provided by the first conveyor 3 can move towards a conveying position by gravitational force. The storage plane 20 may, for example, be sloped by about 5 to about 15 angular degrees relative to horizontal.

The storage plane 20 can have a depth SD chosen such that approximately 10 sample tubes 15 can be placed on the storage plane. In other words, the storage plane can have a buffer capacity of approximately ten sample tubes 15.

The buffer 5 can further comprise a vertical conveyor 22, the vertical conveyor 22 can sequentially load single sample tubes 15 from the conveying position, convey the loaded sample tubes 15 in a vertical direction Z, and sequentially provide the loaded sample tubes 15 to the second conveyor 4 at a given sample tube rate, for example, about 10 to about 200 sample tubes per minute.

The buffer 5 can monitor its buffer level by a suitable sensor, for example, a light barrier, a pressure sensor, a camera, a switch having a switching state depending of the buffer level, and the like. The buffer 5 can cause the sample tube individualizer 2 and the first conveyor 3 to stop if the buffer level exceeds a given upper threshold. If the buffer level falls below a given lower threshold, the sample tube individualizer 2 and the first conveyor 3 can be reactivated and can continue to provide sample tubes 15 to the buffer 5.

The second conveyor 4, like the first conveyor 3, can be formed of two rubber belts 23 and 24.

Figure 3:
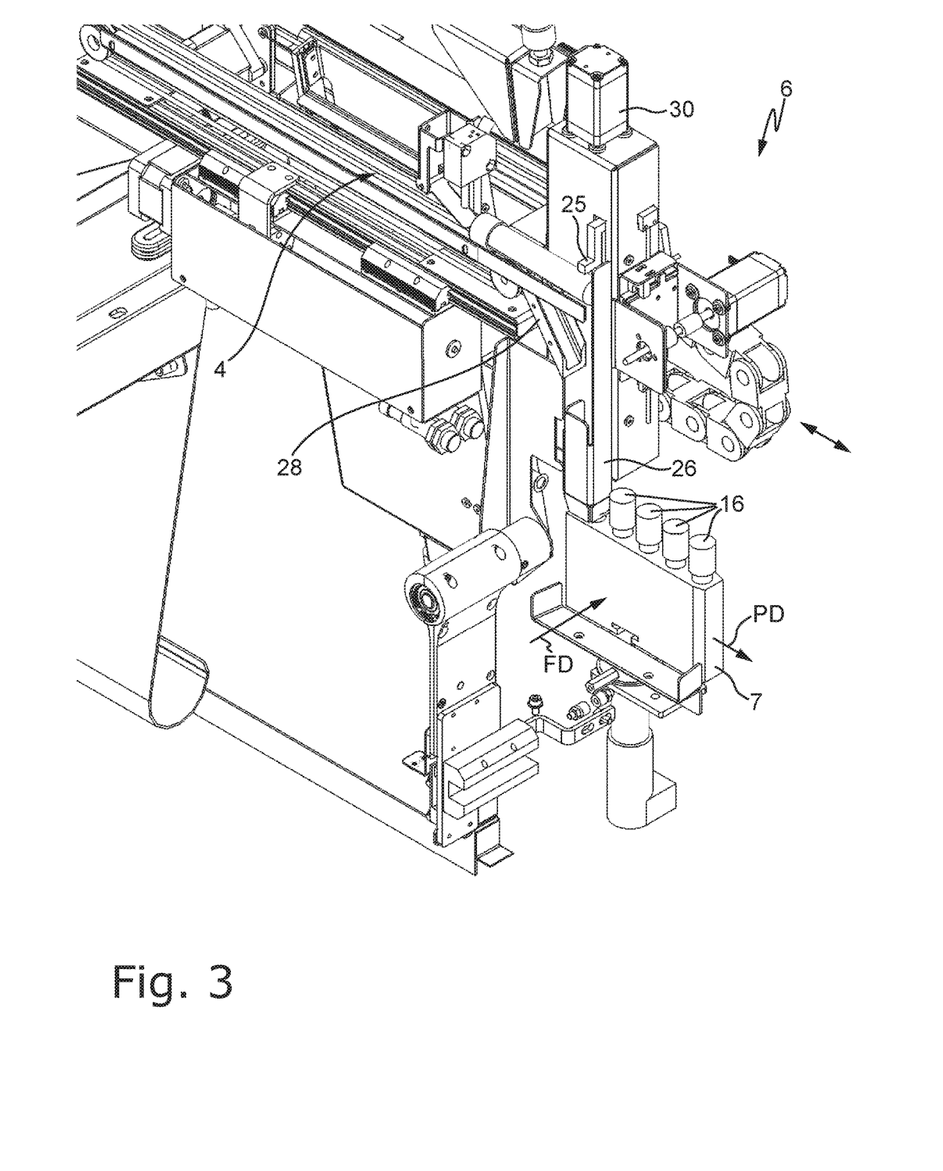
FIG. 3 illustrates the apparatus for handling sample tubes from still another further perspective according to an embodiment of the present disclosure.

The second conveyor can provide the sample tubes 15 to a sample tube rack inserter 6, see FIG. 3. The sample tube rack inserter 6 can insert the sample tubes 15 into a sample tube rack 7.

The sample tube rack inserter 6 can comprise a vertically movable pusher 25 to apply a push force to a cap 16 of a sample tube 15 to be inserted into a corresponding opening of the sample tube rack 7. The pusher 25 can be driven by a stepper motor 30, wherein the pusher 25 and the stepper motor 30 can be mechanically coupled by a shaft (not shown).

The pusher 25 can apply a push force profile to a sample tube 15. At the beginning, a maximum push force can be applied to the sample tube 15. After reaching about 95% of a final insertion position, the push force can be reduced by approximately 100% (i.e. no push force) for about 0.1 seconds. Then about 95% of the maximum push force can be applied to the sample tube 15 until the final insertion position defined by form fit between the sample tube 15 and the sample tube rack 7 is reached.

The sample tube rack inserter 6 can comprise a filling hopper 26 having a vertical opening 27 (see FIG. 5). The hopper 26 can receive sample tubes 15 from the second conveyor 4 and can center the sample tubes 15 with respect to a dedicated opening of sample tube rack 7.

The sample tube rack inserter 6 can further comprise a sloped guide 28 arranged between the second conveyor 4 and the hopper 26. The sloped guide 28 can be sloped such that sample tubes 15 provided by the second conveyor 4 can move towards the hopper 26 by gravitational force.

The second conveyor 4 and the sample tube rack inserter 6 can respectively, horizontally be moved relative to the sample tube rack 7, such that a sample tube 15 can be inserted into a corresponding opening of the sample tube rack 7 without needing to move the sample tube rack 7.

The sample tube racks 7 can be manually or automatically provided from a filling direction FD. After being filled, the sample tube racks 7 can be automatically moved in a processing direction PD rectangular to the filing direction FD.

The apparatus for handling sample tubes can be part of a laboratory (automation) system and can form the front end of the laboratory system. The laboratory system can further comprises laboratory stations such as, for example, decapping stations, aliquot stations, bar code readers, and the like.

The sample tubes 15 can be provided in a completely unsorted bulk commodity. The sample tubes 15 may just be dumped into the sample tube tray 1. The apparatus can efficiently fill the unsorted sample tubes 15 into the sample tube racks 7, such that the laboratory stations may operate rack based. The apparatus can be highly flexible and can offer a high processing performance.

FIG. 6 illustrates an embodiment of a pusher 25 having a specific pushing head 25a. The pushing head 25a can comprise an opening 25c in form of a blind hole to house an upper portion or a cap 16 of a sample tube 15 to be inserted into the sample tube rack 7.

A concave surface 25b can surround the opening or blind hole 25c. The concave surface 25b can guide the upper portion of the sample tube 15 to be inserted into the sample tube rack 7 towards the blind hole 25c such that during an insertion process the upper portion can be reliably guided into the opening 25c. The concave surface 25b surrounding the opening or blind hole 25c can lead to a vertical alignment of the inserted sample tubes 15.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. An apparatus for handling sample tubes, wherein the sample tubes are closed by caps, the apparatus comprising:
    a sample tube tray, wherein the sample tube tray stores sample tubes in bulk commodity;
    a sample tube individualizer, wherein the sample tube individualizer comprises a vertical chain conveyor having a number of chain members, each chain member unloads single sample tubes from the sample tube tray and provides the unloaded sample tubes to a first conveyor;
    the first conveyor, wherein the sample tube individualizer sequentially unloads single sample tubes from the sample tube tray on to a chain member and sequentially provides the unloaded sample tubes to the first conveyor, wherein the sample tubes are provided to the first conveyer such that the sample tubes are initially conveyed in a random conveying direction, the random conveying direction being either the cap first in a conveying direction or the cap last in the conveying direction, and wherein the first conveyor comprises a first belt and a second belt, the first belt and the second belt extending in parallel along a conveying direction and spaced by a given belt distance;
    a second conveyor;
    a sample tube buffer, wherein the sample tube buffer comprises a sloped storage plane and a vertical conveyor, wherein the first conveyor conveys the sample tubes to the sample tube buffer and wherein the sample tube buffer buffers the sample tubes provided by the first conveyor on the sloped storage plane and provides buffered sample tubes to the second conveyor by the vertical conveyor with a predeterminable, constant, sample tube rate;
    a sample tube rack inserter, wherein the second conveyor conveys the sample tubes to the sample tube rack inserter and wherein the sample tube rack inserter is configured to insert the sample tubes into a sample tube rack;
    a conveying direction determiner to determine the conveying direction of a respective sample tube on the first conveyor; and
    a conveying direction changer functionally coupled to the conveying direction determiner and the first conveyor, wherein the conveying direction changer comprises a rotatable leg, the rotatable leg arranged between the first belt and the second belt, the rotatable leg having a width smaller than the given belt distance, and the rotatable leg when rotating changing the conveying direction of a sample tube placed on top of the rotatable leg, and wherein the conveying direction changer is configured to change the conveying direction by rotating the sample tubes along an axis vertically perpendicular to the conveying direction such that each sample tube is provided to the sample tube buffer in a defined conveying direction.

2. The apparatus according to claim 1, wherein the conveying direction changer rotates the rotatable leg with a predetermined rotating speed profile.

3. The apparatus according to claim 1, wherein the sample tube rack inserter comprises a vertically movable pusher, wherein the vertically movable pusher is coupled to a motor and configured to apply a push force to a sample tube to be inserted into a sample tube rack.

4. The apparatus according to claim 3, wherein the vertically movable pusher comprises a pushing head, the pushing head comprising an opening to house an upper portion of the sample tube to be inserted into the sample tube rack, and a concave surface surrounding the opening, the concave surface guides the upper portion of the sample tube to be inserted into the sample tube rack.

5. The apparatus according to claim 3, wherein the vertically movable pusher applies a predetermined push force profile to the sample tube to be inserted into the sample tube rack.

6. The apparatus according to claim 1, wherein the sample tube rack inserter comprises a hopper to receive sample tubes from the second conveyor and to center the sample tubes with respect to a dedicated opening in the sample tube rack.

7. The apparatus according to claim 6, wherein the sample tube rack inserter comprises a sloped guide arranged between the second conveyor and the hopper, wherein the sloped guide is sloped such that sample tubes provided by the second conveyor move towards the hopper by gravitational force.

8. The apparatus according to claim 1, wherein the sample tube rack has two or more openings horizontally spaced for inserting corresponding sample tubes, and the second conveyor and the sample tube rack inserter are respectively horizontally moved relative to the sample tube rack, such that a sample tube is inserted into a corresponding opening of the sample tube rack by a vertically movable pusher of the sample tube rack inserter.

9. The apparatus according to claim 1, wherein the sample tube buffer comprises a sensor, wherein the sensor is configured to monitor a number of sample tubes actually buffered and to signal to the sample tube individualizer and to the first conveyor if more than a given threshold value of sample tubes are actually being buffered, such that the sample tube individualizer and the first conveyor stop operating.

10. The apparatus according to claim 1, wherein the first conveyor and the second conveyor have different vertical levels, wherein the sample tube buffer comprises:
the sloped storage plane, the first conveyor providing sample tubes to the storage plane, the storage plane sloped such that sample tubes provided by the first conveyor move towards a conveying position by gravitational force, the storage plane geometrically dimensioned to store a given number of sample tubes, and
the vertical conveyor, the vertical conveyor sequentially loads single sample tubes from the conveying position, conveys the loaded sample tubes in a vertical direction, and sequentially provides the loaded sample tubes to the second conveyor at the sample tube rate.

11. A laboratory system, the laboratory system comprising:
at least one laboratory station for processing sample tubes and/or samples contained in the sample tubes; and
the apparatus according to claim 1.

12. The laboratory system according to claim 11, wherein the at least one laboratory station is a pre-analytical station, an analytical station, a post-analytical station or combinations thereof.

* * * * *